United States Patent [19]

Mast, Jr.

[11] 4,108,299

[45] Aug. 22, 1978

[54] APPARATUS AND METHOD FOR DELIVERING TAMPON SACKS AND INSERTER PARTS TO AN ASSEMBLY TURRET

[75] Inventor: John George Mast, Jr., Cincinnati, Ohio

[73] Assignee: The Procter & Gamble Company, Cincinnati, Ohio

[21] Appl. No.: 698,274

[22] Filed: Jun. 21, 1976

Related U.S. Application Data

[62] Division of Ser. No. 531,222, Dec. 10, 1974, Pat. No. 4,006,515.

[51] Int. Cl.[2] .............................................. B65G 47/00
[52] U.S. Cl. ...................................... 28/119; 198/479; 28/120
[58] Field of Search .............. 198/480, 481, 608, 803, 198/463, 479, 694, 695, 696; 19/144.5

[56] References Cited

U.S. PATENT DOCUMENTS

| 1,015,319 | 1/1912 | Jefferies et al. | 198/803 X |
| 2,166,381 | 7/1939 | Taylor et al. | 198/696 X |
| 3,460,669 | 8/1969 | Johnson | 198/803 X |
| 3,606,643 | 9/1971 | Mooney | 19/144.5 |

Primary Examiner—John J. Love
Assistant Examiner—Douglas D. Watts
Attorney, Agent, or Firm—Melville, Strasser, Foster & Hoffman

[57] ABSTRACT

Apparatus and procedures for delivering tampon sacks having withdrawal strings at one end and inserter parts to an assembly turret having a plurality of operating heads on which the tampon sacks are assembled in the inserters, the apparatus comprising rotary transfer mechanism for engaging the withdrawal strings of the sacks and sequentially delivering them to a rotary assembly turret having a multiplicity of assembling stations mounted around its periphery. Each inserter comprises inner and outer parts, and feeding means are provided to individually feed and position an inner inserter and an outer inserter in holders at each assembly station.

17 Claims, 21 Drawing Figures

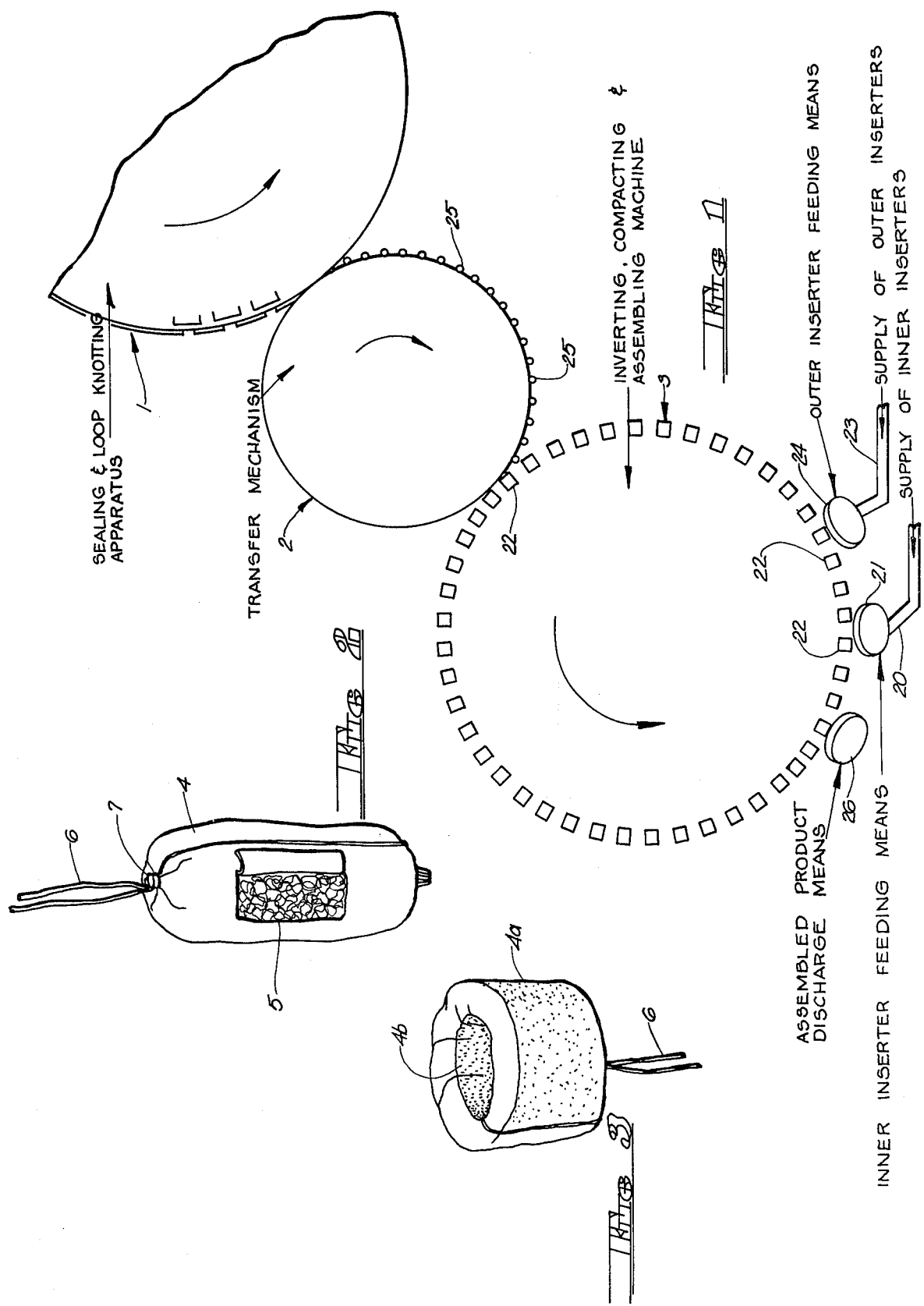

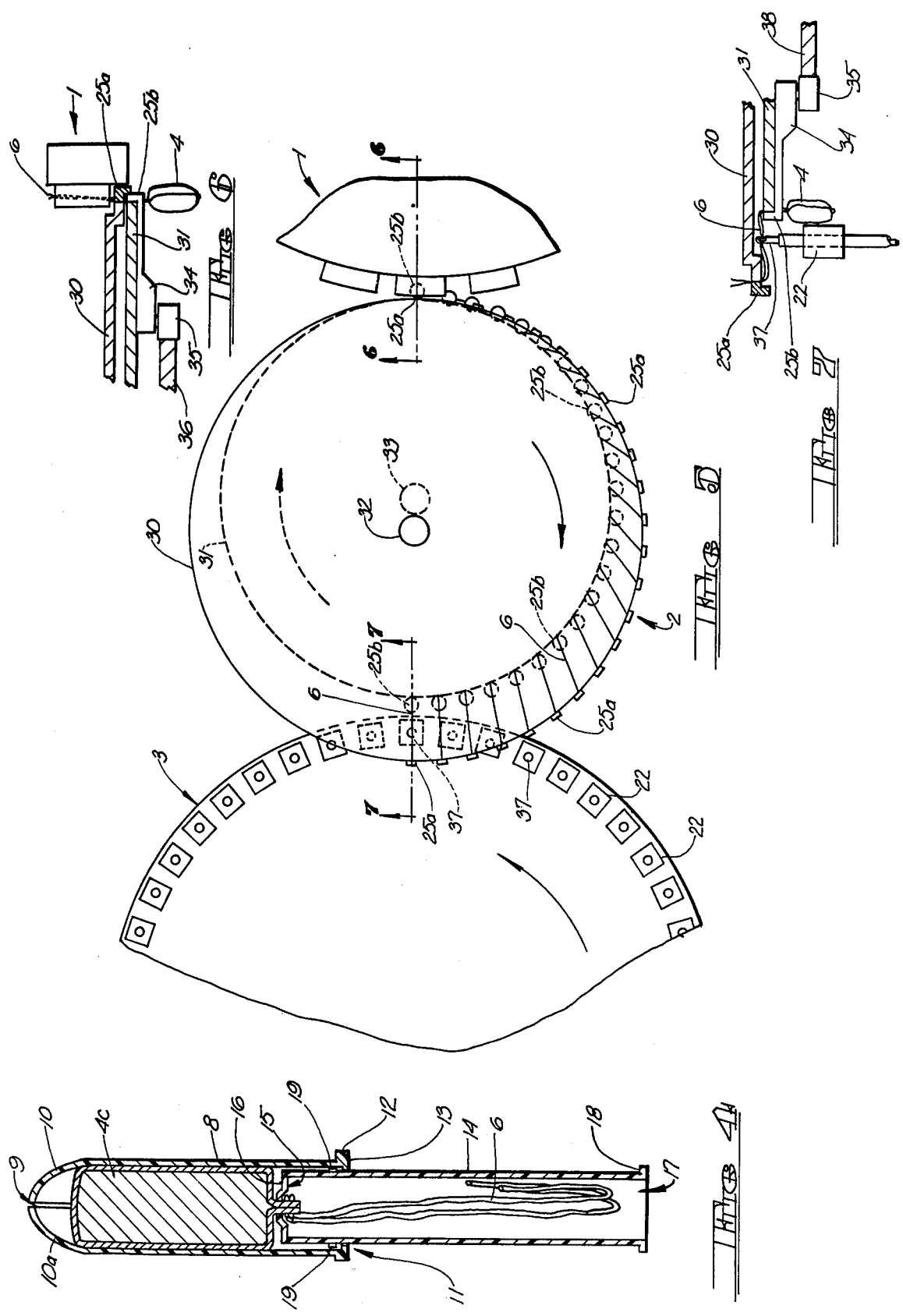

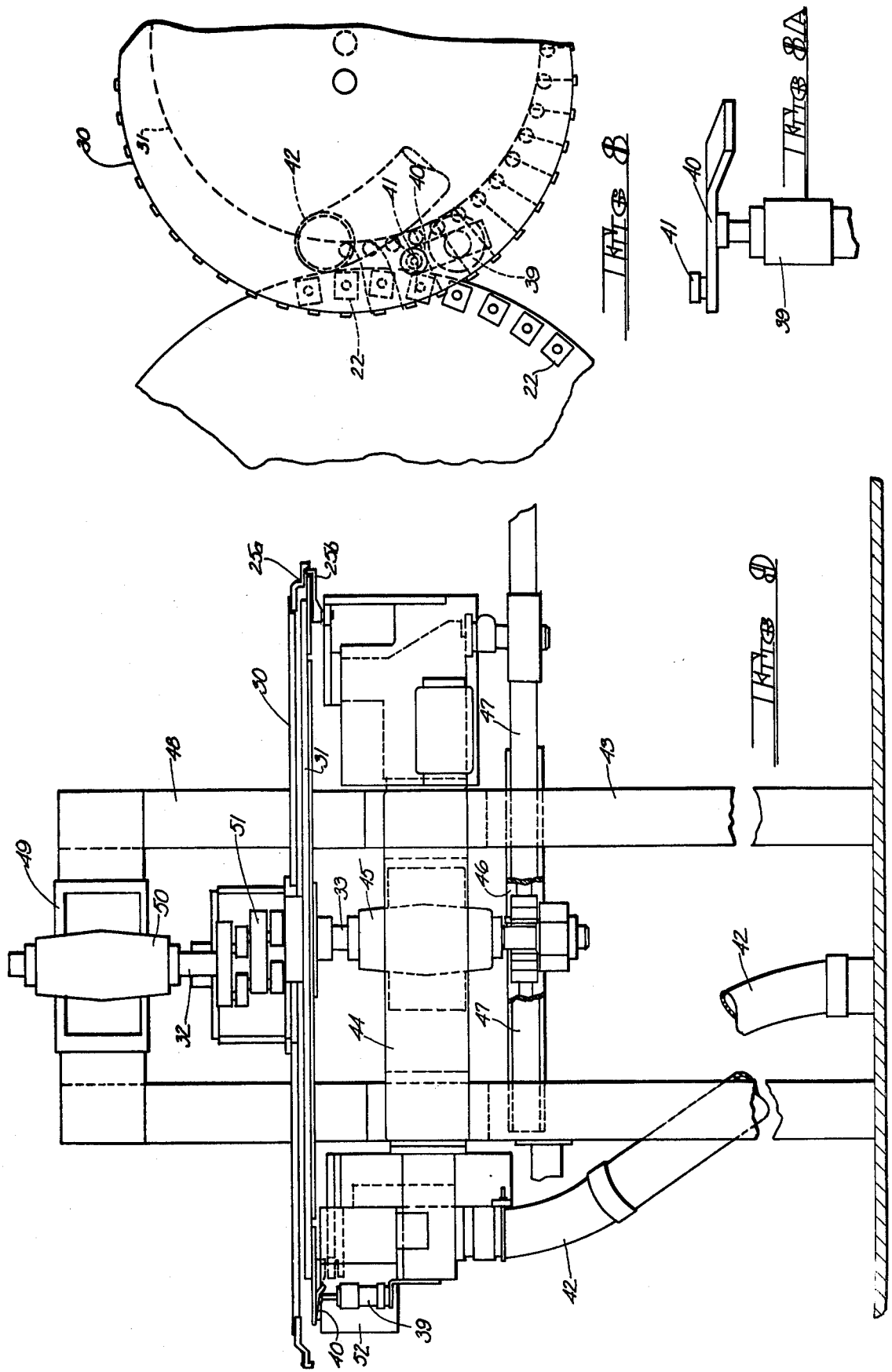

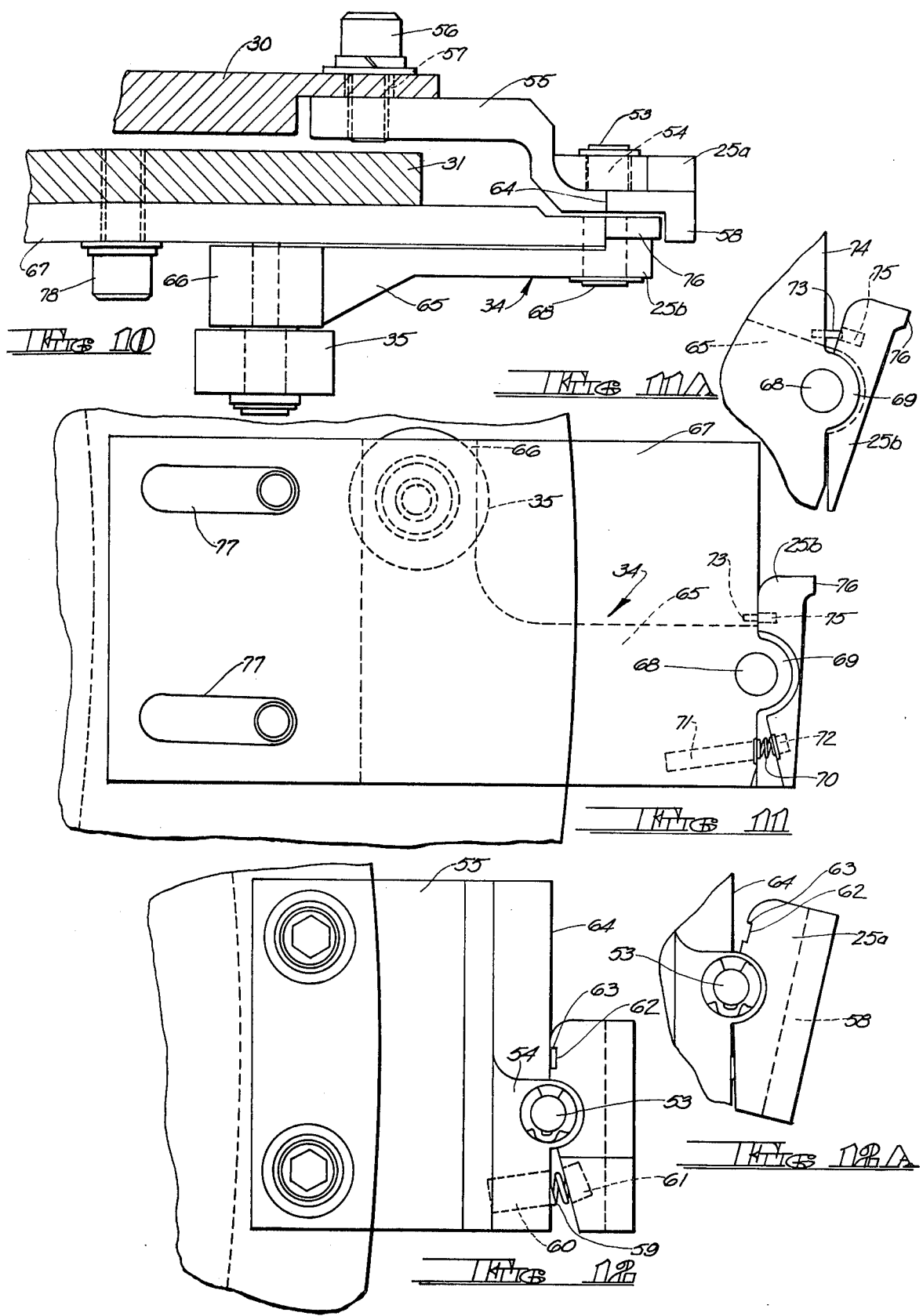

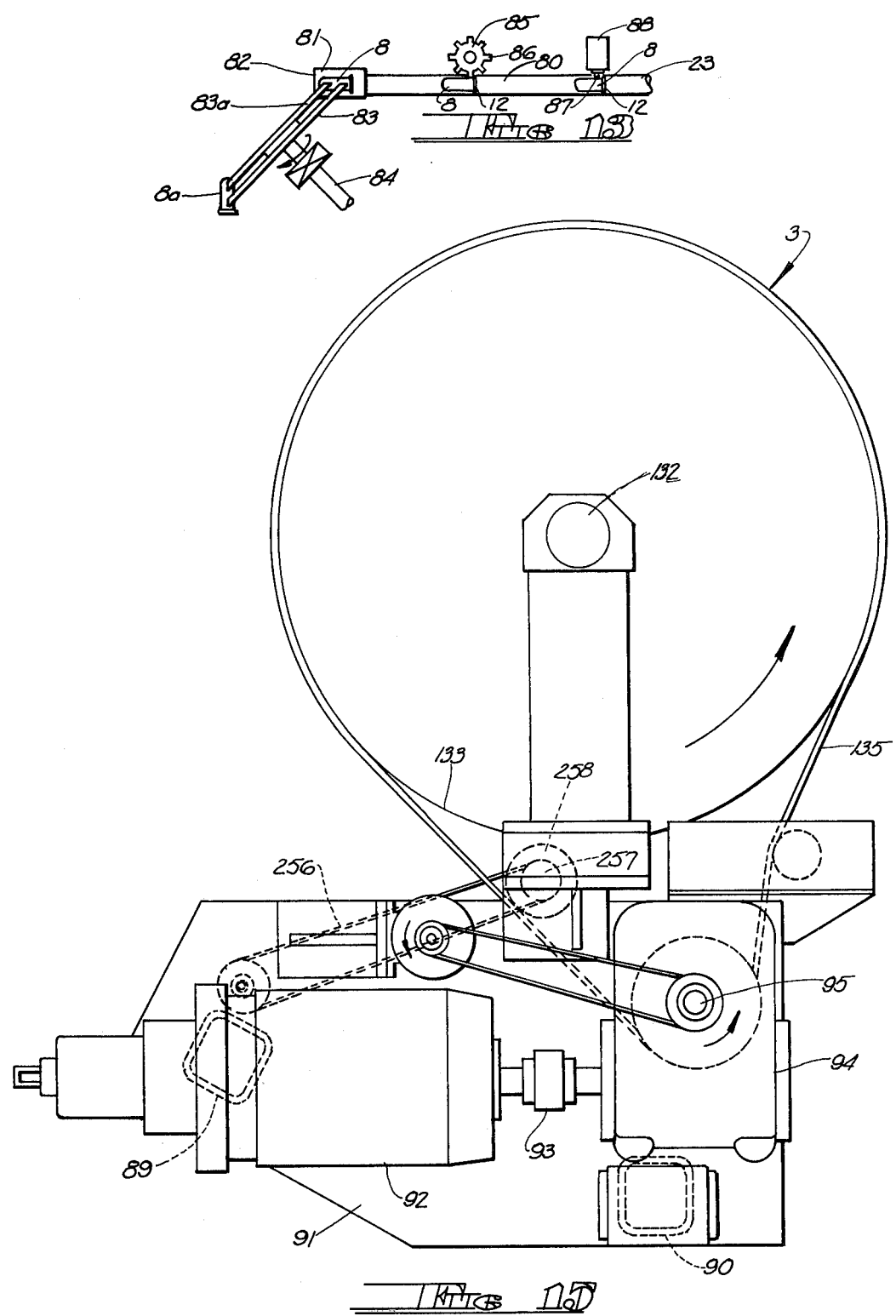

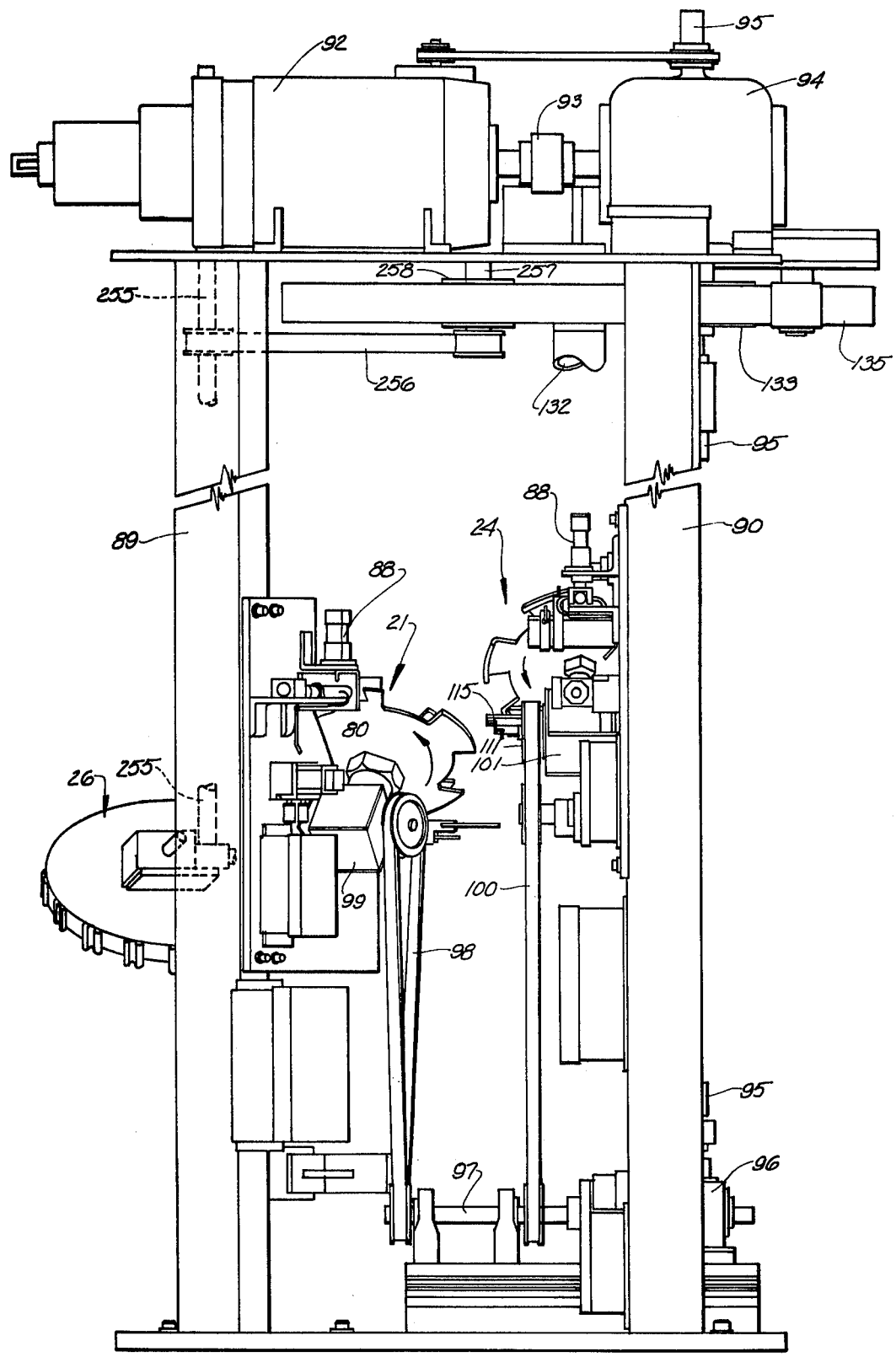

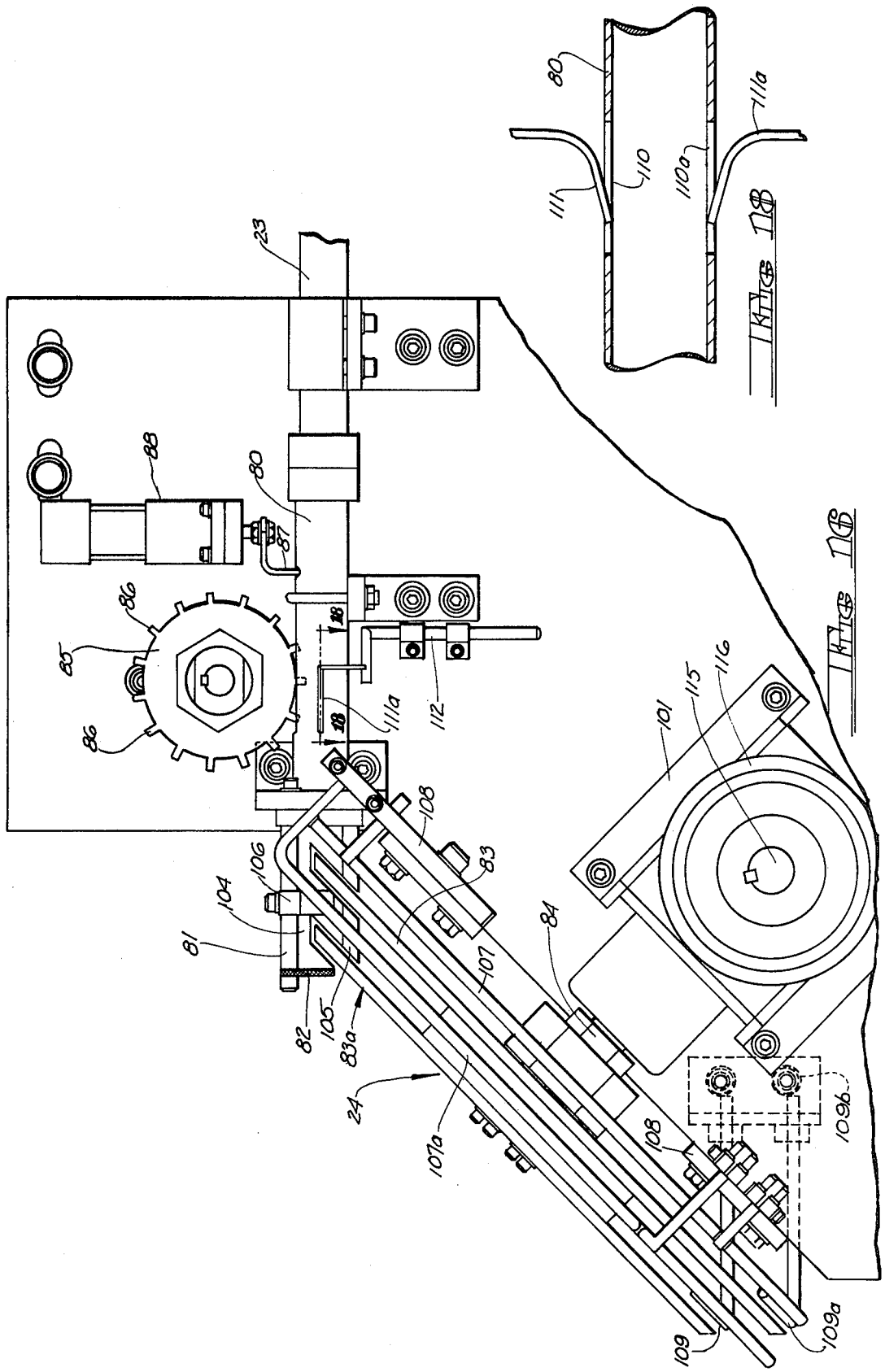

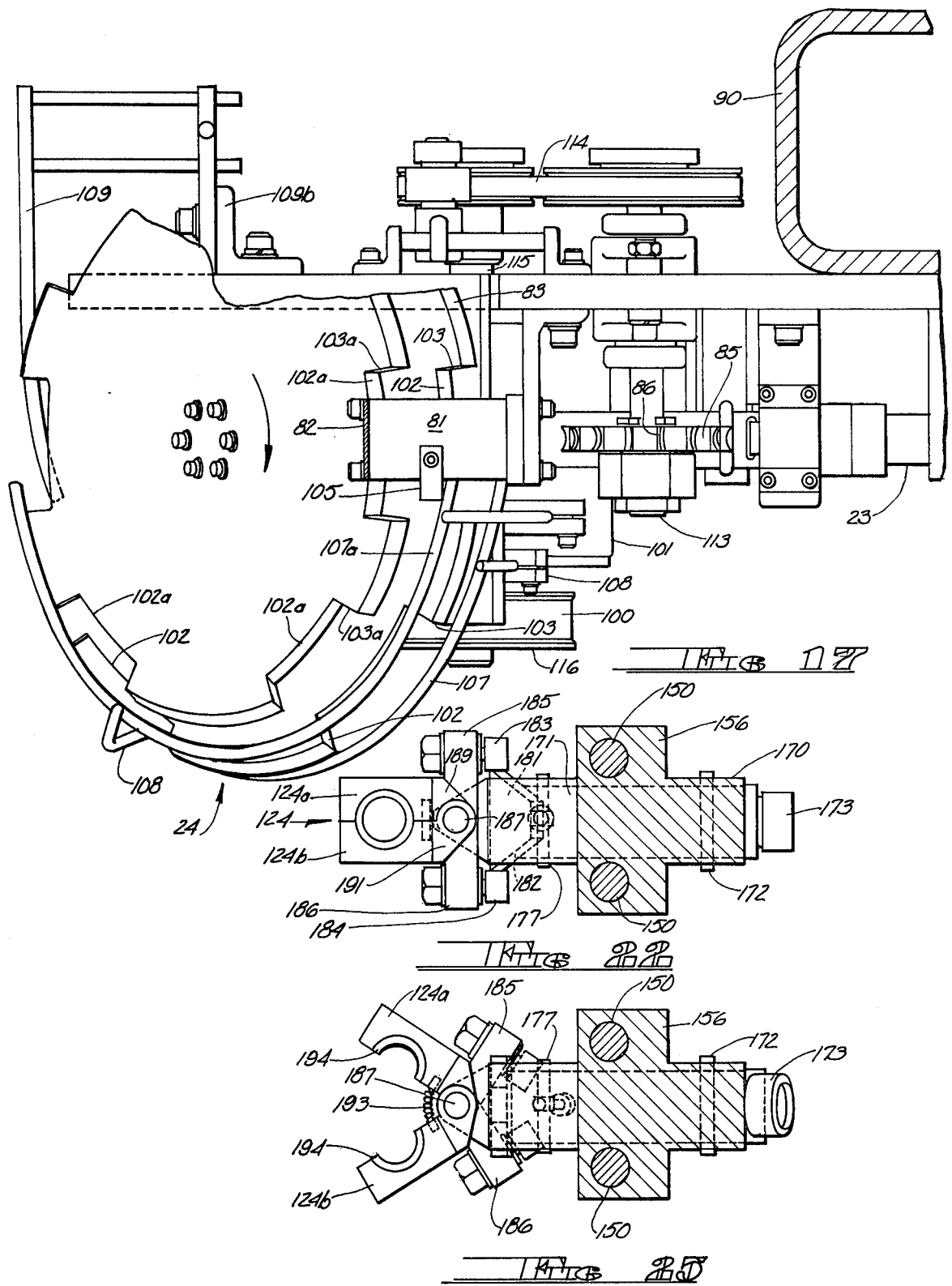

APPARATUS AND METHOD FOR DELIVERING TAMPON SACKS AND INSERTER PARTS TO AN ASSEMBLY TURRET

This is a division of application Ser. No. 531,222, filed Dec. 10, 1974, Now U.S. Pat. No. 4,006,515.

BACKGROUND OF THE INVENTION

1. The Field of Invention

The present invention has to do with the manufacture of tampons and more specifically with the continuous formation of rosette shaped tampons from aggregate containing tubular sacks or overwraps having a withdrawal string at one end, followed by the assembly of the tampons with a two-piece tube-type inserter by means of which the tampon may be inserted into a vagina.

2. Description of the Prior Art

Tampons of the type to which this invention relates are disclosed in commonly owned U.S. Pat. No. 3,815,601, dated June 11, 1974, and entitled "Catamenial Aggregate Absorbent Body". In accordance with the teachings of the said patent, the tampon comprises aggregate composed of individual pieces of absorbent, foam-like material encased within a flexible, fluid-permeable overwrap in the form of a tubular sack closed at its opposite ends, the ends of the sack preferably being gathered inwardly and secured to form end seals. A withdrawal string is attached to one end of the sack, which is preferably elongated, and the sack is inverted to form it into rosette shape by displacing inwardly the distal end of the sack, i.e., the end of the sack opposite the withdrawal string is displaced inwardly to form a cavity in the overwrap, thereby forming a tampon structure in which the absorbent aggregate is encased by an overwrap having an exterior portion forming the exterior surface of the tampon and a re-entrant portion forming the surface of the cavity. Following formation of the tampon into rosette shape, it is radially compressed and enclosed in a tube-type inserter having a head or outer part in which the the tampon is contained and an inner or plunger part by means of which the tampon is expelled from the inserter.

Mechanism and procedures for forming and filling tampon sacks of the character described are disclosed in commonly owned United States Application Ser. No. 484,813, in the name of Jean E. Schaefer, filed July 1, 1974 and entitled "Apparatus And Method For Continuously Forming And Filling Tampon Sacks", now U.S. Pat. No. 3,982,374. In accordance with the teachings of this application, a web of sack forming material is printed with adhesive at spaced apart intervals at which end seals for the sacks are to be formed, the adhesive dried, and the web tubed around a hollow mandrel with the longitudinal edges of the web overlapped and sealed to form the longitudinal seam of the tubing. The tubing is fed to a rotating turret having a purality of pleating and sealing stations which sequentially engage and gather the tubing and seal it together in the areas of the previously applied adhesive to form a continuous series of sacks. As the leading end seal of each successive sack is formed, a charge of aggregate is introduced into the tubing through the mandrel around which it is formed and propelled through the tubing so that the material comes to rest against the leading end seal of the sack being formed, whereupon the formation of the next successive end seal completes the sack and encloses the deposited charge of material. the sacks so-formed may then be provided with withdrawal strings which are stitched or tied to one of the end seals and the sacks cut apart to form individual units.

In another form of apparatus disclosed in commonly owned U.S. Application Ser. No. 517,110 by Ronald W. Kock, filed Oct. 22, 1974 and entitled "Loop Knot Tying Method And Apparatus", now U.S. Pat. No. 3,940,169 the tampon sacks may be fabricated on a rotating device carrying a plurality of operating heads which, in addition to pleating and sealing the web at spaced apart intervals to form sacks, is provided with means for attaching withdrawal strings, including means for metering the correct length of string, cutting the string, piercing the sack in the area of an end seal, forming a loop knot through the pierced hole in the end seal, and severing the sacks intermediate the end seals to provide individual tampon sacks suspended by their withdrawal strings for discharge from the device.

The transfer mechanism of the present invention is specifically designed to engage the strings of tampon sacks fabricated on the apparatus just described and transfer them to the assembly turret for conversion into finished products.

Reference is also made to commonly owned co-pending Application Ser. No. 400,620, by Delmar R. Muckenfuhs, filed Sept. 25, 1973, and entitled "Device And Method For Forming Tampon", now U.S. Pat. No. 3,875,615 which teaches the formation of the closed tubular sacks into rosette shape. A cylindrical holding chamber is provided into which the tubular sack is inserted and expanded radially outwardly by a vacuum drawn on the holding chamber, a reciprocating tubular plunger sequentially acting to guide the sack into the holding chamber, displace the distal end of the sack inwardly to form it into rosette shape, and thereafter eject the shaped tampon from the holding chamber. Aspects of this invention are utilized in, commonly owned copending application Ser. No. 531,222, entitled "Apparatus And Method For Forming Tampons And Assembling Same In Inserters", now U.S. Pat. No. 4,006,515, of which the present application is a division. In accordance with the teachings of this patent, the tampon sacks are delivered by their withdrawal strings to a rotary assembly turret having a multiplicity of assembly stations mounted around its periphery. Each station has a reciprocating string engaging rod which acts to remove a sack by its string from the transfer mechanism and positions the sack to be drawn upwardly by vacuum into an overlying annular inversion chamber wherein the sack is inverted into rosette shape by the action of a pressure-vacuum reciprocating inversion rod. The shaped sack is then moved downwardly into an underlying compression cone wherein it is radially compressed and drawn downwardly into an underlying cylindrical compression chamber, whereupon the outer inserter is positioned to overlie the compression chamber and the inner inserter, which underlies the compression chamber, is moved upwardly by a reciprocating assembly rod which causes the inner inserter to push the compacted tampon upwardly into the overlying outer inserter, and at the same time the upper end of the inner inserter engages within the outer inserter to complete the assembly. The assembled inserter is then transferred from the assembly station to a discharge wheel for delivery to a collection station or other mechanism for wrapping, packaging, or the like as the rotary assembly turret completes its cycle of operation.

The inserter delivery mechanism of the present invention is designed to deliver the inner and outer inserter parts to the assembly stations described above, the mechanism serving to deposit the inserter parts in holders mounted on the assembly stations.

SUMMARY OF THE INVENTION

In accordance with the invention, an integrated system is provided for receiving the tampon sacks in filled and closed condition, with withdrawal string attached, orienting the string in predetermined position and presenting the string for engagement by the assembly turret which mounts a plurality of heads or stations each of which utilizes vacuum, low pressure air and a number of mechanical motions to invert the sack, compress the inverted sack and assemble it with an inserter having inner and outer parts, the system also including feeder units for delivering the inner and outer inserters to the assembly turret and positioning them at each station, together with a discharge mechanism for removing the completed product from the assembly turret.

The transfer mechanism for receiving and delivering the tampon sacks to the assembly turret comprises a transfer wheel having top and bottom discs each mounting about its periphery coacting sets of string gripping jaws which grasp the withdrawal string at two closely spaced apart points. The top and bottom discs of the transfer wheel are mounted on different centers and, as the wheel rotates, the upper and lower sets of gripping jaws in each set move toward and away from each other. The sets of gripping jaws are in vertical alignment when the withdrawal string is initially engaged, whereupon the jaws begin to move away from each other causing the string to be partially pulled through the looser top jaw so as to suspend the string substantially horizontally between the jaws as they approach the assembly turret. The horizontally disposed string runs into a vertical string grabber rod on the assembly turret which opens just prior to the string reaching it, and snaps shut as soon as the string is in its clamping jaw, whereupon the lower gripping jaw opens to release the string and the assembly turret pulls the string from the open lower gripping jaw and out of the closed upper jaw. The transfer mechanism also incorporates means for rejecting unwanted tampon sacks comprising a reject pin movable into the path of the horizontally disposed string just before transfer to the assembly turret. The reject pin engages the string and pulls it out of the upper gripper jaw resulting in the bag being held only by the lower gripping jaw, which makes transfer to the assembly turret impossible. When the lower gripping jaw opens after transfer should have taken place, the rejected sack falls into a reject chute.

The inner and outer inserters are separately fed to the assembly turret by feeder wheels which are of essentially identical construction, the inserter parts being fed to their respective feeder wheels by air flowing through conveyor tubes which deliver the inserter parts horizontally in nose to tail relation. The parts are separated from the conveying air flow by a screen which readily passes the air but stops the nose of the conveyed part in proper position for transfer by the feeder wheel. Upon engagement by the feeder wheel, the inserter is accelerated sideways and turned through an angle of 90° to bring it up to a surface speed and position matching a station on the assembly turret, whereupon it is pushed into a holder by rails or sweeps when the part is in vertical alignment with a station on the turret. In the case of the feeder for the outer inserters, it is preferred to provide an escapement wheel to hold the second inserter back while the first is being engaged and moved sideways by the feeder wheel to prevent damage to the nose portions of the outer inserters which have resilient pedals which deflect outwardly as the tampon is ejected. Since the noses of the inner inserters are relatively flat and do not have fragile petals, an escapement wheel is not required for the inner inserters. Each feeder is also provided with high pressure air jets to speed up the movement of the inserters into the feeder wheel, and gate means are provided to prevent the feeding of inserters when they are not needed.

DESCRIPTION OF THE DRAWINGS

FIG. 1 is a diagrammatic plan view illustrating the general organization of apparatus in accordance with the invention.

FIG. 2 is a perspective view with parts broken away of a tampon sack prior to formation into rosette shape.

FIG. 3 is a perspective view showing the tampon sack after formation into rosette shape.

FIG. 4 is a vertical sectional view of the compacted tampon assembled in a two-piece tube type inserter.

FIG. 5 is a diagrammatic plan view illustrating the general operation of the transfer mechanism.

FIG. 6 is an enlarged vertical sectional view taken along the line 6—6 of FIG. 5.

FIG. 7 is an enlarged vertical sectional view taken along the line 7—7 of FIG. 5.

FIG. 8 is a fragmentary diagrammatic plan view illustrating the operation of reject means utilized in conjunction with the transfer mechanism.

FIG. 8A is an enlarged fragmentary perspective view of the reject means.

FIG. 9 is a side elevational view of the transfer mechanism broken away.

FIG. 10 is an enlarged side elevational view of a set of upper and lower gripping jaws for the transfer mechanism.

FIG. 11 is a plan view illustrating the details of the lower gripping jaw assembly, with the jaw in closed position.

FIG. 11A is a fragmentary plan view similar to FIG. 11 illustrating the lower gripping jaw in open position.

FIG. 12 is a plan view illustrating the details of the upper gripping jaw assembly, with the jaw in closed position.

FIG. 12A is a fragmentary plan view similar to FIG. 12 illustrating the upper gripping jaw in open position.

FIG. 13 is a diagrammatic side elevational view illustrating the operation of the inserter feeding means.

FIG. 14 is a side elevational view of the inserter feeding means and the drive means for the various components.

FIG. 15 is a top plan view of the drive means shown in FIG. 14.

FIG. 16 is an enlarged partial side elevational view of the outer inserter feeding means.

FIG. 17 is a plan view, with parts broken away, of the inserter feeding means shown in FIG. 16.

FIG. 18 is an enlarged vertical sectional view taken along the line 18—18 of FIG. 16 illustrating the air jets for the inserter feeding means.

DESCRIPTION OF THE PREFERRED EMBODIMENTS

General Organization

For a general understanding of the organization and operation of the apparatus, reference is first made to FIG. 1 of the drawings wherein reference numeral 1 indicates mechanism by means of which tubular tampon sacks are suspended by their withdrawal strings and presented for transfer by the rotary transfer mechanism 2 to the rotary inverting, compacting and assembly machine 3, which will be referred to as the assembly turret. Preferably, the mechanism 1 will comprise sealing and loop knotting apparatus of the character described in the aforementioned commonly owned application Ser. No. 517,110, now U.S. Pat. No. 3,940,169 which fabricates the tampon sacks and attaches their withdrawal strings, the tampon sacks so-formed being suspended by their withdrawal strings for discharge from the device. It is to be understood, however, that the apparatus by means of which the tampon sacks are formed and their withdrawal strings attached, does not constitute a part of the present invention, but rather is merely indicative of apparatus which will present the suspended tampon sacks to the transfer mechanism 2 which forms a part of the present invention and comprises the means of which the tampon sacks are delivered in timed relation to the movement of the assembly turret 3.

A tampon sack of the type which will be delivered to transfer mechanism 2 is illustrated in FIG. 2, the structure comprising a tubular sack or overwrap 4 containing an aggregate 5 composed of individual pieces of absorbent foam-like material which is loosely encased within the overwrap. A withdrawal string 6 is securely attached to one end of the overwrap, as at the end closure 7. While in the embodiment illustrated the withdrawal string engages the end closure at approximately its mid-point and hence has two free end portions, it is deemed herein to comprise a single withdrawal string since it functions as a single irrespective of whether it has one or two free ends.

One of the functions of the assembly turret 3 is to form the tampons into rosette shape by inverting the sacks to assume the condition illustrated in FIG. 3. As seen therein, the tampon structure has a generally cylindrical body defined by the exterior portion 4a and a generally conical re-entrant portion defined by the interior portion 4b, the structure in the condition illustrated being ready for radial compaction and insertion into a tube type inserter, which compacting the assembly operation are also performed on the assembly turret 3.

The completed and assembled tampon and inserter is illustrated in FIG. 4, the compacted, rosette shaped tampon, indicated at 4c, being contained within the upper portion of a tubular outer inserter part 8 having a nose 9 which is defined by a plurality of petals, two of which are indicated at 10 and 10a, which flex outwardly to permit discharge of the tampon from the inserter. At its trailing end 11, the outer inserter has a plurality of non-connected gripping elements 12 which may terminate inwardly in a stop shoulder 13 to engage the cylindrical wall surface of the inner inserter part 14 which is of tubular configuration, having a leading or nose end 15 defined by an annular shoulder 16 through which the withdrawal string 6 passes, the inner inserter terminating at its trailing end 17 in an annular flange 18. The inner inserter also may be provided with detents 19 which coact with the cylindrical wall surface of the outer inserter 8 and with its stop shoulder 13 to maintain the inner and outer inserter parts in assembled condition. In use, the inner inserter 14 acts as a plunger to discharge the tampon through the nose of the outer inserter.

Referring again to FIG. 1, a supply of inner inserters 14 is delivered to the assembly turret 3 through conduit means 20, such as an air-conveying system, from a source of supply (not shown). The inner inserters are sequentially fed by the rotary feeding means 21 to each of the operating heads or stations 22 on the assembly turret at which the inserting, compacting and assembling operations take place. Similarly, a supply of outer inserters 8 is fed through conduit means 23 to the rotary feeding means 24 which sequentially delivers an outer inserter to each of the heads 22 as the assembly turret rotates. Transfer of the tampon sacks from the transfer mechanism 2 to the assembly turret 3 takes place as the heads 22 come into tangential relation with the transfer mechanism, which mounts sets of jaws,, indicated generally at 25, which position the withdrawal strings for engagement by a string grabber forming a part of each operating head 22.

As each of the operating heads 22 proceeds beyond the transfer mechanism 2, the inverting, compacting and assembly of the tampon structures and their inserters takes place, the assembled structures being removed from the assembly turret 3 by the rotary discharge means 26, whereupon the operating cycle of the machine is completed and the heads again pass the rotary feeding means 21 to commence another operating cycle.

The Transfer Mechanism

For a general understanding of the transfer mechanism 2, reference is made to FIG. 5 of the drawings which diagrammatically illustrates its operation, the transfer mechanism comprising a wheel assembly having an upper rotary disc 30 and a lower or underlying rotary disc 31 which is of smaller diameter, the upper disc 30 having an axis of rotation indicated by the shaft 32, whereas the axis of rotation of the lower disc, indicated by the shaft 33, is displaced laterally relative to the shaft 32, the arrangement being such that the peripheries of the upper and lower discs will be effectively in vertical alignment at their point of nearest approach to the mechanism 1 from which the tampon sacks are suspended, and will be spaced apart by the greatest distance at their point of the nearest approach to the assembly turret 3.

Each of the sets of jaws 25 comprises an upper jaw 25a mounted on the periphery of the upper disc 30 and a coacting lower jaw 25b mounted on the periphery of lower disc 31. As possible best seen in FIG. 6, as each set of jaws approaches the mechanism 1, the upper and lower jaws will be in vertical alignment and will be jointly opened as the withdrawal string 6 of a tampon sack suspended from the mechanism 1 is presented to the jaws, whereupon the jaws are closed in clamping engagement with the withdrawl string, the opening and closing movement of the jaws being effected by the action of cam means 34 having cam roller 35 in contact with a cam track 36. The speed of rotation of the transfer mechanism will be somewhat slower than the mechanism 1, and the upper and lower jaws will be positioned so that the withdrawal strings will overrun the open jaws and will be drawn into the jaws just prior to their closing.

The engagement between the upper jaw 25a and the withdrawal string 6 will be sufficiently loose to permit slippage of the string relative to the jaw, whereas the lower jaw is in tight clamping engagement with the withdrawal string. With this arrangement, as the discs rotate toward the assembly turret 3, the upper and lower jaws in each set will move apart and, in so moving, the withdrawal string 6 will be partially pulled through the looser top jaw so as to draw each string into essentially horizontal position as it approaches the assembly turrent, such drawing apart of the strings being illustrated in FIG. 5.

Each withdrawal string is thus horizontally disposed as it is presented to an operating head 22 on the assembly turret, and the speed of rotation of the discs 30 and 31 relative to the assembly turret will be such that the string will overrun the station 22 and, in so doing, the string may be readily engaged by a string grabbing means 37 forming a part of each head 22, as possibly best seen in FIG. 7. Once the withdrawal string 6 has been engaged by the string grabbing means 37, the lower jaw 25b will be opened by the action of a cam track 38 positioned to engage the cam follower 35, thereby releasing the tampon sack from the lower disc 31. Since the withdrawal string is loosely engaged by the upper jaw 25a, the remainder of the string will be pulled from the upper jaw as the rotation of the parts continues, the withdrawal string now being firmly and tightly engaged by the string grabbing means 37.

The transfer mechanism also incorporates means for removing the tampon sacks from the transfer mechanism in the event transfer to the assembly machine cannot be accomplished. As seen in FIGS. 3 and 8A, a fluid cylinder or solenoid 39 is mounted beneath the lower disc 31, the cylinder in turn mounting an arm 40 carrying an upstanding reject button 41 movable from a lowermost or inoperative position to an elevated or operating position in which it extends into the path of travel of an advancing withdrawal string, thereby forming an obstruction which engages the string and causes its free end to be pulled from the upper clamping jaw 25a, which is outermost, the withdrawal string thus being held solely by the innermost lower clamping jaw 25b. As will be evident, upon being pulled from the upper clamping jaw 25a, the string will dangle and no longer will be horizontally disposed and hence no longer positioned to be engaged by the string grabbing means 37. Consequently, at the point where the lower jaw 25b is opened by the action of cam track 38, which occurs just after the string grabber means 37 would have engaged the string had it been in normal operating position, the release of the string by the lower gripping jaw results in the tampon being dropped into an underlying reject chute 42, to thereby collect the rejected tampon sacks.

With the foregoing general description of the transfer mechanism in mind, reference is now made to FIG. 9 for a more detailed description. The transfer mechanism is mounted on a supporting frame 43 having an extension 44 which mounts a hub 45 in which the shaft 33 for the lower disc 31 is rotatably journaled, the shaft being driven through gear belt pulley 46 and gear belt 47 which may be connected to a source of power, although preferably the transfer mechanism will be driven by the sealing and loop knotting mechanism 1, the drive belt 47 being operatively connected to the drive means (not shown) for the latter mechanism, suitable protective means, such as an overload clutch being provided to guard the transfer mechanism from damage in the event of jams. Alternatively, the transfer mechanism may be driven from the assembly turret 3 or by a separate synchronized motor.

The supporting frame 43 includes an upper portion 48 lying to one side of the discs 30 and 31 which mounts a lateral extension 49 having a hub 50 in which the upper drive shaft 32 is rotatably journaled, the shaft 32 being driven from shaft 33 by means of a Schmidt coupling 51 which, as will be understood by the worker in the art, comprises a linkage which carries torque from one parallel shaft to another.

As seen in FIG. 9, the arm 40 mounting reject pin 41 is in its lower or inoperative position, but upon energization of the fluid cylinder 39 will be displaced upwardly to engage the withdrawal strings of the sacks to be rejected. The reject chute 42 may be conveniently provided at its upper end with a funnel-like deflector, indicated at 52, positioned to receive the rejected tampons upon their release by the lower gripping jaws 25b and deflect them downwardly into the reject chute 42.

Referring next to FIG. 10 which illustrates the relationship of the gripping jaws and their component parts, the upper jaw 25a is pivotally connected by pivot pin 53 to the hub-forming portion 54 of mounting plate 55 by means of which the upper jaw is secured to the upper rotating disc 30, attachment bolts 56 being provided to secure the mounting plate to the rotatable disc, preferably through slot-like openings 57 in the rotary disc which permits adjustment of the position of the clamping jaw 25a relative to the center of the upper disc 30. The gripping jaw 25a has a depending shoulder or flange 58 which forms an abutment for moving the gripping jaw 25a from the closed position illustrated in FIG. 12 to the open position illustrated in FIG. 12A. The jaw 25a is normally biased to the closed position by spring 59 the opposite ends of which are received in pockets 60 and 61 formed in the mounting plate 55 and jaw 25a, respectively. A shallow recess 62 is provided on jaw 25a adjacent its free end, which terminates in a shoulder 63 coacting with the vertical edge 64 of the mounting plate 55 to clamp the withdrawal string in the recess 62 when the jaw is in the closed position. Since the upper gripping jaw 25a loosely grips the string, the clamping pressure exerted by spring 59 will be only sufficient to hold the string in the recess 62 between the jaw 25a and the vertical edge 64 of the support plate.

The lower gripping jaw 25b is an integral part of the cam means 34 referred to in connection with FIGS. 6 and 7, which cam means comprises a rearwardly projecting arm 65 (seen in FIGS. 10 and 11) having a lateral extension 66 which mounts the cam roller 35. The cam means 34, including the gripping jaw 25b, is pivotally connected to a mounting plate 67 by means of a pivot pin 68 projecting downwardly from an extending ear 69 forming part of mounting plate 67 into the underlying arm 65 of which the jaw 25b is an integral part. A spring 70 normally biases the clamping jaw 25b to the closed position, the spring being received at one end in a pocket 71 in the mounting plate 67 and at its opposite end in a pocket 72 in the clamping jaw. The guide pin 73 projects outwardly from the vertical edge 74 of the mounting plate 67, and is adapted to be received in a mating recess 75 in the lower jaws 25b. With this arrangement, the guide pin 73 lies in close proximity to the ear 69 and is of a length such that it effectively forms a stop for the string, i.e., when the jaw 25b is closed, the string is effectively clamped between the vertical edge 74 of the mounting plate 57 and the opposing surface of jaw 25a lying outwardly beyond guide pin 73.

In operation, when the cam roller 35, which is operatively connected to the lower jaw 25b, contacts cam track 36 to effect opening movement of the jaws, it will be evident that as the cam track 36 presses against the cam roller 35, the unitary assembly comprising the lower gripping jaw 25b, the rearwardly projecting arm 65 and lateral extension 66, will pivot about pivot pin 68, thereby pivoting the lower jaw to the open position illustrated in FIG. 11A. It will be noted that the lower jaw 25b has a projecting tip 76 which, as will be evident from FIG. 10, lies immediately inwardly of the depending shoulder 58 of upper jaw 25a. Thus, when the lower jaw 25b is moved from its closed to its open position, the projecting tip 76 will press against the depending flange 58 of upper jaw 25a and concurrently move the upper jaw to the open position. Of course, as soon as the cam roller 35 is released by its cam track, both jaws will be freed to return to their closed positions under the influence of their respective springs, thereby clamping the withdrawal string between them.

While a separate cam rail 38 at the opposite side of the transfer mechanism serves to reopen the lower clamping jaws 25b as the strings are engaged by the string grabbers on the assembly turret, such opening movement will have no effect on the upper gripping jaws since the upper jaws are spaced laterally from the lower jaws and hence out of position to be actuated by the lower jaws.

The mounting plates 67 for the lower jaws are provided with elongated slots 77 by means of which they are mounted on the rotary disc 31, as by means of mounting bolts 78. The slots 77 are relatively long so that the sets of gripping jaws just described may be utilized to handle strings of different lengths, which may be readily accomplished by changing the position of shaft 33 mounting the lower disc 31, the elongated slots in the lower mounting plates 67 permitting a wide latitude of adjustment to bring the lower jaws into vertical alignment with the upper jaws at the point where the strings are received from the mechanism 1.

INSERTER FEEDING MEANS.

Reference is next made to FIG. 13 for a general description of the operation of the inserter feeder means. While the illustration is directed specifically to the feeder means for the outer inserters 8, it is to be understood that the feeding means for the inner and outer inserters are essentially identical in construction and operation except for specific differences hereinafter noted.

The conduit means 23 through which the outer inserters 8 are delivered terminates in a tubular discharge section 80 having a holder 81 at its far end, the holder having a screen 32 defining its remote end which will readily pass the air utilized to advance the inserters but will stop the nose of each inserter in proper position for engagement by a feeder wheel composed of inner disc 83 and outer disc 83a which, as the wheel rotates, engages each inserter and accelerate it sideways up to a surface speed and position matching an operating head on the assembly turret. The feeder wheel receives the inserters in a horizontal position and turns them through an angle of 90° by the action of the 45° drive shaft 84, the inserters being presented to the assembly turret in vertically disposed position, as indicated by the inserter 8a in FIG. 13.

In the case of the inner inserters 14, they will travel through the discharge section 80 in nose to tail relation, successively entering the holder 81 as the preceding inserter is engaged and moved sideways by the feeder wheel 83, such sideways movement releasing the next succeeding inserter for movement into the holder 81. However, in the case of the outer inserters 8, which have relatively fragile petals at their nose end, an escapement wheel 85 is provided in discharge section 80 to hold back a second inserter while the first is being moved sideways by the feeder wheel, since it is this sideways movement which causes damage to the petals of the outer inserters if they are in nose to tail relation. The lugs 86 on the escapement wheel 85 are preferably positioned to engage the gripping elements 12 on the trailing ends of the inserters. Both the inner and outer inserter feeding means are provided with retractable gates 87 controlled by a solenoid or fluid cylinder 88 to shut-off the supply of inserters to the feeding wheels as may be required during start-up or adjustment of the apparatus.

Referring next to FIG. 14 for a more defined description, the feeder means 21 for the inner inserters is mounted on a vertical support 89, and the feeding means 24 for the outer inserters is mounted on a vertical support 90, the supports 89 and 90 also serving as supports for an overhead platform 91 which mounts the prime mover 92 from which the various operating components are driven. A coupling 93 connects the prime mover to a gear reducer 94 to which a vertical line shaft 95 is connected to carry torque down to a right angle gear box 96 which drives the horizontal drive shaft 97. The drive shaft 97 is connected by drive belt 98 to the gear box 99 for the inner inserter feeding means 21, and the shaft is connected by drive belt 100 to the gear box 101 which drives the outer inserter feeding means 24.

Referring next to FIG. 17 which, while specifically illustrating the feeding means 24, is essentially identical in construction and operation to the feeding means 21, except for the differences previously noted. Thus, the gear box 101 drives the feeder wheel drive shaft 84 to thereby drive the inner and outer discs 83 and 83a which are fixed to the shaft for joint rotation therewith. As possibly best seen in FIG. 17, the inner and outer discs 83 and 83a have aligned sets of elongated slots 102 and 102a having trailing shoulders 103 and 103a which, as the discs pass through the holder 81, engage and move sideways an inserter positioned in the holder 81 with its nose against screen 82. As possibly best seen in FIG. 16, the holder 81 has a slotted far side wall 104 and a slotted bottom wall 105 through which the feeder wheel segments 83 and 83a pass, the rear or trailing side of the holder 81 being open except for a depending spring finger 106 which acts to press and align the inserters with respect to the traling shoulders 103 and 103a as the inserters are moved sideways out of the holder. The inserters are held in the slots 102 and 102a by the curved hold-down rods 107 and 107a mounted on spaced apart brackets 108 which act to maintain the inserters in the slots 102 and 102a as the discs rotate, the hold-down rods maintaining the inserters in the slots until they have been uprighted, i.e., brought to a vertical position at their point of closest approach to the assembly turret. As the inserters approach the vertical position, they are engaged by stripping rods 109 and 109a mounted on bracket 109b, the stripping rods acting to discharge the inserters from the feeder wheel as the inserters pass beyond the terminal ends of hold-down rods 107 and 107a. As will become apparent hereinafter, as the inserters are stripped from the feeder, the stripping rods 109 and 109a will press them into holders forming a part of each head on the assembly turret.

While the inserters will be delivered to the discharge section 80 by means of air under pressure which carriers the inserters through their respective feed conduits, it is preferred to provide additional air jets to accelerate the movement of the inserters into the holder 81. To this end, and as illustrated in FIG. 18, slots 110 and 110a are formed in the opposite sides of the discharge section 80 into which air jets 111 and 111a project, the air jets facing in the direction of the holder 81 and serving to accelerate the inserters as they move toward their respective holders. In the case of the feeder means 24 for the outer inserters, which includes the escapement wheel 85, the air jets are positioned to impinge upon the inserters as they are released by the escapement lugs 86. Air under pressure may be supplied to the jets 111 and 111a through a common feed tube 112.

As shown in FIGS. 14 and 17, the escapement wheel 85 for the feeder means 24 may be driven by a drive shaft 113, the opposite end of which is connected through drive belt 114 to a shaft 115 driven by drive belt 100, the shaft 115 mounting pulley wheel 116 which is engaged by drive belt 100, the shaft 115 mounting pulley wheel 116 which is engaged by drive belt 100, the shaft 115 thus driving both the gear box 101 and the escapement wheel 85.

As should now be apparent, the present invention provides integrated apparatus and procedures for delivering tampons and inserters to an assembly turret in a continuous high speed operation. In its apparatus aspects, the invention contemplates the various components by means of which the tampon sacks and the inserter parts are delivered to the assembly turret; and in its method aspects, the invention contemplates the techniques and procedures by means of which the tampon sacks and inserters are delivered to the assembly turret.

Numerous modifications of the invention have already been set forth, and additional modifications and variations will undoubtedly occur to the worker in the art upon reading this specification, and it is therefore not intended that the scope of the invention be limited other than in the manner set forth in the claims which follow.

The embodiments of the invention in which an exclusive property or privilege is claimed are defined as follows:

1. Apparatus for feeding tampon inserters to a tampon assembly turret, a rotatable feeder wheel inclined at an angle of substantially 45°, said wheel comprising spaced inner and outer discs having mating sets of slots therein, drive means for rotating said wheel, holder means overlying said feeder wheel for feeding inserter parts to said wheel, said holder means having a slotted bottom positioned to receive the inserter parts and align them for engagement by the sets of slots in said inner and outer discs, said discs passing through the slotted bottom of said holder means, coacting hold-down rods positioned to maintain the inserter parts in said sets of slots, and mens for transferring the inserter parts from said wheel to the assembly turret.

2. The apparatus claimed in claim 1 wherein the inserter parts are conveyed to said holder means through a conveyor tube by air under pressure, said holder means having a perforated end wall positioned to stop the inserters in alignment with said sets of slots while passing the air under pressure therethrough.

3. The apparatus claimed in claim 2 including a tubular discharge section connecting said holder means to the conveyor tube for the inserter parts, and air jet means in said discharge section positioned to accelerate movement of the inserter parts into said holder means.

4. The apparatus claimed in claim 3 including an escapement wheel having lugs positioned to engage and restrain movement of successive inserter parts through said tubular discharge section, and means for driving said escapement wheel in timed relation to the rotation of said feeder wheel.

5. Apparatus for delivering tampon sacks to an assembly turret comprising a rotatable transfer wheel comprising upper and lower discs mounted for joint rotation about different axes of rotation, one of the discs being larger than the other, the axes of the discs being positioned relative to each other so that the peripheries of the discs will be substantially in vertical alignment at one point in their paths of rotation, means for rotating said transfer wheel, a plurality of string gripping means mounted at equally spaced apart intervals about the periphery of each of said discs, said string gripping means being arranged in upper and lower sets and having jaws movable from closed to opened position, and means for sequentially opening and closing said jaws.

6. The apparatus claimed in claim 5 wherein the means for opening and closing said jaws comprises cam means operatively connected to one of the jaws in each set, and means operatively connecting the jaw to which said cam means is connected to the other jaw in said set, whereby the jaws in each set will be simultaneously opened and closed by said cam means.

7. A method for delivering a tampon sack having a withdrawal string at one end to a tampon assembly turret, comprising the steps of suspending the tampon sack by its string with the string in vertical position, engaging the string at a pair of closely spaced apart gripping points near one end of the string, moving the tampon sack in a horizontal path of travel and, as an incident of such movement, displacing the gripping points laterally with respect to each other to draw the string into an essentially horizontal position for presentation to the turret.

8. The method claimed in claim 7 including the step of tightly clamping the string at the point closest to the nearest end of the string, and loosely clamping it at the other point, whereby as the gripping points are displaced laterally with respect to each other, the string will be pulled through the point at which it is loosely engaged.

9. In apparatus for forming tampons and assembling them in inserters wherein tampon sacks having withdrawal strings at one end and inserter parts are delivered in timed relation to a rotary assembly turret having a plurality of operating heads on which the tampon sacks are shaped into cylindrical configuration and assembled in the inserters, a rotary feeder wheel for delivering inserter parts to the operating heads on said turret, drive means for rotating said feeder wheel in timed relation to the rotation of said assembly turret, holder means for feeding inserter parts to said feeder wheel, means for maintaining the inserter parts in contact with said feeder wheel, and means for transferring the inserter parts from said feeder wheel to the operating heads on said assembly turret; a rotatable transfer wheel for delivering tampon sacks to the operating heads on said assembly turret, means for rotating said transfer wheel in timed relation to the rotation of said assembly turret, a plurality of spring gripping means mounted at equally spaced apart intervals about the periphery of said transfer wheel for gripping the strips of the tampon sacks presented thereto, said string gripping means having jaws movable from closed to open position, and means for sequentially opening and closing said jaws in timed relation to the rotation of said transfer wheel between a station at which the tampon sacks are presented to said string gripping means and the delivery of said tampon sacks to said assembly turret, said jaws being closed upon the presentation of the string of a tampon sack thereto and opened upon presentation of the tampon sack to an operating head on said assembly turret.

10. The apparatus claimed in claim 9 wherein said feeder wheel comprises spaced apart inner and outer discs, wherein the means for maintaining the inserter parts in contact with said wheel include mating sets of slots in said inner and outer discs, and coacting holddown rods positioned to maintain the inserter parts in said sets of slots.

11. The apparatus claimed in claim 10 wherein said holder means overlies said feeder wheel and has a slotted bottom positioned to receive the inserter parts and align them for engagement by the sets of slots in said inner and outer discs, said inner and outer discs passing through the slotted bottom of said holder means.

12. The apparatus claimed in claim 11 wherein the inserter parts are conveyed to said holder means through a conveyor tube, means for introducing air under pressure into said conveyor tube, said holder means having a perforated end wall positioned to stop the inserters in alignment with said sets of slots while passing the pressurized air therethrough.

13. The apparatus claimed in claim 9 wherein said transfer wheel comprises upper and lower discs mounted for joint rotation about spaced apart axes of rotation, one of said discs being larger than the other, the axes of the discs being positioned relative to each other so that the peripheries of said discs will be substantially in vertical alignment as said discs approach the station at which the strings of the tampon sacks are presented to said string gripping means, said discs each mounting string gripping means about its periphery, said string gripping means being arranged in mating upper and lower sets.

14. The apparatus claimed in claim 13 wherein the means for opening and closing the jaws of said string gripping means comprises cam means operatively connected to one of the jaws in each set of string gripping means, and means operatively connecting the jaw to which said cam means is connected to the jaw of the other string gripping means in said set, whereby the jaw in each set will be simultaneously opened and closed by said cam means.

15. The apparatus claimed in claim 14 including means cooperating with one of the jaws in each set to cause said jaw to enter into tight clamping engagement with the withdrawal string of a tampon sack engaged thereby, and means associated with the other jaw in the set to loosely engage the withdrawal string.

16. The apparatus claimed in claim 15 wherein said cam means includes means operative to open the jaw which tightly clamps the withdrawal string as the jaw passes its point of nearest approach to said assembly turret.

17. The apparatus claimed in claim 16 wherein the clamping jaws in each set are spaced apart laterally as the said set of jaws approaches the assembly turret, whereby the portion of the withdrawal string extending between the set of jaws is essentially horizontally disposed for presentation to an operating head on said assembly turret.

* * * * *

UNITED STATES PATENT AND TRADEMARK OFFICE
CERTIFICATE OF CORRECTION

PATENT NO. : 4,108,299
DATED : August 22, 1978
INVENTOR(S) : John George Mast, Jr.

It is certified that error appears in the above-identified patent and that said Letters Patent are hereby corrected as shown below:

Column 5, line 27, "of" should read --by--.

Column 5, lines 51-52, "operation" should read --operations--.

Column 9, line 2, "57" should read --67--.

Column 9, line 58, "32" should read --82--.

Column 11, Claim 1, line 65, "mens" should read --means--.

Column 13, Claim 9, line 5, "spring" should read --string--.

Column 13, Claim 9, line 9, "strips" should read --strings--.

Signed and Sealed this

Fifteenth Day of May 1979

[SEAL]

Attest:

RUTH C. MASON
Attesting Officer

DONALD W. BANNER
Commissioner of Patents and Trademarks